(12) United States Patent
Wuellner et al.

(10) Patent No.: US 8,558,005 B2
(45) Date of Patent: Oct. 15, 2013

US008558005B2

(54) METHODS FOR THE PRODUCTION OF 2-HALO-4-NITROIMIDAZOLE AND INTERMEDIATES THEREOF

(75) Inventors: Guido Wuellner, Leverkusen (DE); Franz-Willi Herkenrath, Hennef (DE); Alexander Juelich, Leverkusen (DE); Yoshinori Yamada, Tokyo (JP); Shuji Kawabe, Tokyo (JP)

(73) Assignees: Dynamit Nobel GmbH Explosivstoff-und Systemtechnik, Leverkusen (DE); Asahi Kasei Chemicals Corporation, Tokyo (JP); Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/059,333

(22) PCT Filed: Aug. 21, 2009

(86) PCT No.: PCT/JP2009/065015
§ 371 (c)(1),
(2), (4) Date: Apr. 12, 2011

(87) PCT Pub. No.: WO2010/021409
PCT Pub. Date: Feb. 25, 2010

(65) Prior Publication Data
US 2011/0178308 A1  Jul. 21, 2011

(30) Foreign Application Priority Data

Aug. 21, 2008  (JP) .................................. 2008-212868
Aug. 21, 2008  (JP) .................................. 2008-212873
Aug. 21, 2008  (JP) .................................. 2008-213053
Aug. 21, 2008  (JP) .................................. 2008-213057
Jun. 10, 2009  (WO) .................. PCT/IB2009/005911

(51) Int. Cl.
*C07D 233/68* (2006.01)
*C07D 233/91* (2006.01)

(52) U.S. Cl.
USPC ..................................... 548/335.5; 548/343.1

(58) Field of Classification Search
USPC ........................................... 548/335.5, 343.1
See application file for complete search history.

(56) References Cited

U.S. PATENT DOCUMENTS 5,387,297 A   2/1995   Damavarapu et al.

FOREIGN PATENT DOCUMENTS

EP   1 720 838 B1   11/2006
WO   WO 2006/035960 A2   4/2006

OTHER PUBLICATIONS

Suwinski, et al., "Nitroimidazoles, Part V*. Chloronitroimidazoles From Dinitroimidazoles. A Reinvestigation**", Polish Journal of Chemistry, vol. 56, pp. 1261-1272, (1982).*
Bulusu et al, J. Phys. Chem., (1995), vol. 99, No. 14, pp. 5009-5015.*
Suwinski, et al., "Nitroimidazoles, Part V*. Chloronitroimidazoles From Dinitroimidazoles. A Reinvestigation**", Polish Journal of Chemistry, vol. 56, pp. 1261-1272, (1982).*
Suwinski, et al., "Nitroimidazoles, Part V*. Chloronitroimidazoles From Dinitroimidazoles. A Reinvestigation**", Polish Journal of Chemistry, vol. 56, pp. 1261-1272, (1982).*
International Search Report from the European Patent Office in International Application No. PCT/JP2009/065015 mailed Dec. 23, 2009.
Grimmett, et al., "1-4 Dinitroimidazole and Derivatives. Structure and Thermal Rearrangement", Australian Journal of Chemistry, An Australian Journal of Scientific Research, vol. 42, No. 8, pp. 1281-1289, (1989).
Suwinski, et al., "Nitroimidazoles. Part IX*. Some Reactions of 1, 4-Dinitroimidazoles", Polish Journal of Chemistry, vol. 61, No. 7-12, pp. 913-920, (1987).
Suwinski, et al., "Nitroimidazoles, Part V*. Chloronitroimidazoles From Dinitroimidazoles. A Reinvestigation**", Polish Journal of Chemistry, XP009048285, vol. 56, pp. 1261-1272, (1982).
Novikov, et al, Khim. Geterotski. Soedin., No. 4, pp. 503-507, (1970).
Bulusu, et al., "Thermal Rearrangement of 1,4-Dinitroimidazole to 2, 4-Dinitroimidazole: Characterization and Investigation of the Mechanism by Mass Spectrometry and Isotope Labeling", J. Phys. Chem, vol. 99, No. 14, pp. 5009-5015, (1995).

* cited by examiner

*Primary Examiner* — Kamal Saeed
*Assistant Examiner* — Janet L Coppins
(74) *Attorney, Agent, or Firm* — Finnegan, Henderson, Farabow, Garrett & Dunner, L.L.P.

(57) ABSTRACT

The present invention relates to a method for the production of 2-halo-4-nitroimidazole and intermediates thereof. Further, the present invention relates to a production process of 1,4-dinitroimidazole comprising subjecting 4-nitroimidazole to nitration reaction. Furthermore, the present invention relates to a production process of 4-nitroimidazole comprising subjecting imidazole to nitration reaction.

35 Claims, No Drawings

METHODS FOR THE PRODUCTION OF 2-HALO-4-NITROIMIDAZOLE AND INTERMEDIATES THEREOF

TECHNICAL FIELD

The present invention relates to a method for the production of 2-halo-4-nitroimidazole and intermediates thereof. Further, the present invention relates to a production process of 1,4-dinitroimidazole comprising subjecting 4-nitroimidazole to nitration reaction. Furthermore, the present invention relates to a production process of 4-nitroimidazole comprising subjecting imidazole to nitration reaction.

BACKGROUND ART 2-halo-4-nitroimidazole is a compound useful as an intermediate notably for the synthesis of various medicines or pesticides. In particular, it is useful as intermediate for the production of an antituberculous agent.

There is a need to develop efficient and economic methods for the production of these compounds.

NON-PATENT DOCUMENT 1 discloses a method for producing 1,4-dinitroimidazole by reacting 4-nitroimidazole in acetic acid with nitric acid. 1,4-dinitroimidazole is then extracted with the aid of dichloromethane. There is no disclosure as to how to produce 2-halo-4-nitroimidazole.

NON-PATENT DOCUMENT 2 discloses a synthesis of 1,4-dinitroimidazole by reacting nitroimidazole in glacial acetic acid with fuming nitric acid, followed by the addition of acetic anhydride. The resulting compound is then extracted from the solution with the aid of ethylene chloride. NON-PATENT DOCUMENT 2 also discloses a step of heating 1,4-dinitroimidazole at 120° C. to obtain 2,4-dinitroimidazole. There is no disclosure as to how to produce 2-halo-4-nitroimidazole.

PATENT DOCUMENT 1 discloses a process for the production of 2,4-dinitroimidazole. In a first step 1,4-dinitroimidazole is produced, by the reaction of 4-nitroimidazole in glacial acetic acid with nitric acid, in the presence of acetic anhydride. The compound is then precipitated and filtered. In a second step 2,4-dinitroimidazole is produced by heating 1,4-dinitroimidazole in chlorobenzene. The obtained yield can be calculated and is rather low (63%).

NON-PATENT DOCUMENT 3 discloses the preparation of 2,4-dinitroimidazole by thermal isomerization of 1,4-dinitroimidazole. The document also discloses (in relation to another reaction) the preparation of 2-chloro-4-nitroimidazole and 2-bromo-4-nitroimidazole by reacting 2,4-dinitroimidazole with respectively concentrated hydrochloric acid and concentrated hydrobromic acid under reflux. But the yields are rather low (2-chloro-4-nitroimidazole 67%; 2-bromo-4-nitroimidazole 30%).

PATENT DOCUMENT 2 discloses a method for the production of 2-chloro-4-nitroimidazole or 2-bromo-4-nitroimidazole comprising the iodination of 4-nitroimidazole and then the reduction of the obtained compound.

PATENT DOCUMENT 3 discloses a method for the production of 2-chloro-4-nitroimidazole comprising the reaction of 1-alkoxyalkyl-2-bromo-4-nitroimidazole with hydrogen chloride.

As for conventional production process of 2-chloro-4-nitroimidazole or 2-bromo-4-nitroimidazole, 1,4-dinitroimidazole (II) obtained by nitrating 4-nitroimidazole (I) was isolated and dried. Subsequently, 2,4-dinitroimidazole (III) obtained by thermal rearrangement of 1,4-dinitroimidazole (II) is isolated and dried, and finally 2,4-dinitroimidazole (III) is treated with hydrochloric acid or hydrobromic acid to obtain 2-chloro-4-nitroimidazole (IV) or 2-bromo-4-nitroimidazole (V) in the known synthetic processes.

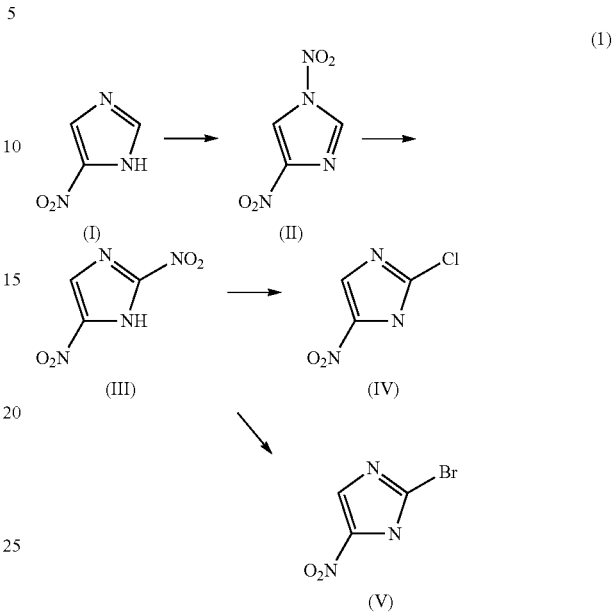

(1)

As for a production process of 1,4-dinitroimidazole from 4-nitroimidazole, a production process of 2,4-dinitroimidazole from 1,4-dinitroimidazole, a production process of 2-chloro-4-nitroimidazole or 2-bromo-4-nitroimidazole from 2,4-dinitroimidazole, processes described in the following documents (PATENT DOCUMENT 1 and NON-PATENT DOCUMENTS 3 to 5) are known.

As a production process of 1,4-dinitroimidazole from 4-nitroimidazole, in NON-PATENT DOCUMENT 4, 4-nitroimidazole is added to acetic acid and nitric acid having a specific gravity of 1.5 is added dropwise thereto, and then acetic anhydride is added to perform nitration reaction. Then the reaction solution is extracted with dichloromethane and the dichloromethane layer is washed with a saturated sodium hydrogen carbonate aqueous solution and dichloromethane is evaporated under reduced pressure to produce 1,4-dinitroimidazole at a yield of 71.5%.

In NON-PATENT DOCUMENT 5, 100 mass % nitric acid is added dropwise to 4-nitroimidazole in glacial acetic acid and acetic anhydride is further added dropwise thereto to perform nitration reaction, and then the reaction solution is added into crushed ice and 1,4-dinitroimidazole is produced at a yield of 52.1% by performing filtration, washing and vacuum drying.

In PATENT DOCUMENT 4, 98 mass % nitric acid is added dropwise to 4-nitroimidazole dissolved in glacial acetic acid and acetic anhydride is further added dropwise thereto to perform nitration reaction, and then the reaction solution is added into crushed ice and 1,4-dinitroimidazole is produced at a yield of 69.1% by performing filtration and drying.

In addition, as a production process of 2,4-dinitroimidazole from 1,4-dinitroimidazole, in NON-PATENT DOCUMENT 5, isolated and dried 1,4-dinitroimidazole is subjected to thermal rearrangement reaction in chlorobenzene at 115° C. and then the solution is concentrated and crystallized. Subsequently, crystals are filtered and vacuum dried at 60° C. or less to produce 2,4-dinitroimidazole at a yield of 87.5%.

In NON-PATENT DOCUMENT 3, isolated and dried 2,4-dinitroimidazole is refluxed with hydrochloric acid or hydrobromic acid to perform chlorination or bromination reaction, and 2-chloro-4-nitroimidazole and 2-bromo-4-nitroimidazole are produced respectively at a yield of 67% and 30%.

In PATENT DOCUMENT 4, isolated and dried 1,4-dinitroimidazole is subjected to thermal rearrangement reaction by heating in a range of 95 to 98° C. to produce 2,4-dinitroimidazole.

As for conventionally employed common processes for synthesizing 2-chloro-4-nitroimidazole, a process described in the following NON-PATENT DOCUMENT 3 is known.

In NON-PATENT DOCUMENT 3, after concentrated hydrochloric acid is added to 2,4-dinitroimidazole, the resultant solution is refluxed for 3 hours to perform chlorination reaction, and 2-chloro-4-nitroimidazole is produced at a yield of 67% by performing cooling, filtration and washing.

1,4-Dinitroimidazole is a substance widely used as intermediates of various medicinal drugs, agricultural agents and explosives. As for conventionally employed common processes for synthesizing 1,4-dinitroimidazole, processes described in the following documents (NON-PATENT DOCUMENTS 4 and 5, and PATENT DOCUMENT 1) are known.

In NON-PATENT DOCUMENT 4,4-nitroimidazole is added to acetic acid and nitric acid having a specific gravity of 1.5 is added dropwise thereto, and then acetic anhydride is added to perform nitration reaction. Then the reaction solution is extracted with dichloromethane, the dichloromethane layer is washed with a saturated sodium hydrogen carbonate aqueous solution and dichloromethane is evaporated under reduced pressure to produce 1,4-dinitroimidazole at a yield of 71.5%. Here, according to *Kagaku Binran Kisohen II* edited by The Chemical Society of Japan, the concentration in term of mass % of the nitric acid having a specific gravity at 25° C. of 1.5 is in a range of 82 to 100 mass % when rounding off the hundredth number of the specific gravity. According to this, it can be understood that the concentration of the nitric acid used in NON-PATENT DOCUMENT 4 is in a range of 82 to 100 mass %.

In NON-PATENT DOCUMENT 5, 100 mass % nitric acid is added dropwise to 4-nitroimidazole in glacial acetic acid and acetic anhydride is further added dropwise thereto to perform nitration reaction, and then the reaction solution is added into crushed ice and 1,4-dinitroimidazole is produced at a yield of 52.1% by performing filtration, washing and vacuum drying.

In PATENT DOCUMENT 1, 98 mass % nitric acid is added dropwise to 4-nitroimidazole dissolved in glacial acetic acid and acetic anhydride is further added dropwise thereto to perform nitration reaction, and then the reaction solution is added into crushed ice and 1,4-dinitroimidazole is produced at a yield of 69.1% by performing filtration and drying.

As for conventional processes for nitrating imidazole (I) to obtain 4-nitroimidazole (II), processes described in the following documents (NON-PATENT DOCUMENTS 4 and 5) are known.

In NON-PATENT DOCUMENT 4, nitric acid is added to imidazole at 30 to 40° C., and then concentrated sulfuric acid is added dropwise to this solution while the solution is ice-cooled and the temperature is elevated to 75° C. and the solution is stirred for 1 hour. Then the solution is cooled and a mixed solution of nitric acid and concentrated sulfuric acid is added thereto. The solution is heated and stirred for another hour and the reaction liquid is poured into ice and 4-nitroimidazole is produced at a yield of 73% by performing filtration, washing and drying.

In NON-PATENT DOCUMENT 5, after imidazole is dissolved in nitric acid, the resultant solution is cooled to 0 to 5° C. and concentrated sulfuric acid is added dropwise thereto. After this solution is refluxed for 2 hours, the solution is cooled to room temperature and then poured into ice, and 4-nitroimidazole is produced at a yield of 60% by performing filtration, washing and drying.

CITATION LIST

Patent Documents

[PATENT DOCUMENT 1] U.S. Pat. No. 5,387,297
[PATENT DOCUMENT 2] EP Patent No. 1-720838
[PATENT DOCUMENT 3] WO 2006035960 A Non Patent Documents

[NON-PATENT DOCUMENT 1] Grimmett et al., Aust. J. Chem., 42, 1281, 1989
[NON-PATENT DOCUMENT 2] Suwinski et al., Polish Journal of Chemistry, "Nitroimidazoles, Part IX", XI, 61, 913, 1987
[NON-PATENT DOCUMENT 3] Jerzy SUWINSKI, Ewa SALWINSKA, Jan WATRAS and Maria WIDEL, Polish Journal of Chemistry, 56, 1261-1272 (1982)
[NON-PATENT DOCUMENT 4] Novikov S. S., Khemel' nitskii L. I., Lebedev O. V., Sevast' yanova V. V., Epishina L. V., Khim. Geterotski. Soedin., No. 4, 503-507 (1970)
[NON-PATENT DOCUMENT 5] S. Bulusu, R. Damavarapu, J. R. Autera, R. Behrens, Jr., L. M. Minier, J. Villanueva and Jayasuriya, T. Axenrod, J. Phys. Chem. 99, 5009-5015 (1995)

SUMMARY OF INVENTION

Technical Problem

Firstly, the object of the present invention is to provide a more efficient method for the production of 2-halo-4-nitroimidazole than the existing methods.

Secondly, the results from the present inventors' estimation on the safety of 1,4-dinitroimidazole and 2,4-dinitroimidazole are shown in Table 1. The present inventors estimated heat stability of 1,4-dinitroimidazole by DSC, and the results revealed that the decomposition starting temperature of 1,4-dinitroimidazole was 156° C., which means that 1,4-dinitroimidazole has a significantly low decomposition temperature and thus poor heat stability. In addition, 1,4-dinitroimidazole was judged to be the second grade in drophammer sensitivity test according to JIS K 4810 of, and it was confirmed to be highly sensitive. It can be understood from this that it is extremely difficult to secure enough safety in the handling of dry solid of 1,4-dinitroimidazole.

In addition, the decomposition temperature of 2,4-dinitroimidazole is 272° C. which is considered to be thermally stable but since the decomposition heat thereof is as high as 4076 J/g, which is a calorific value comparable to those of explosives, it might generate serious damage if it should be decomposed and exploded by a shock and the like.

TABLE 1

| Compound name | Molecular formula | Decomposition temperature $T_{DSC}$ [°C.] | Decomposition heat $Q_{DSC}$ [J/R] | Drop hammer sensitivity [grade] | Friction sensitivity [grade] | Ignition property | Fifth class Test |
|---|---|---|---|---|---|---|---|
| 1,4-dinitro-imidazole (II) | $C_3H_3N_4O_4$ | 156 | 1311 | 2 | 7 | Not determined | Not determined because of high danger |
| 2,4-dinitro-imidazole (III) | $C_3H_2N_4O_4$ | 272 | 4076 | 7 | 6 | Not ignited | 5-II |

All the synthetic processes described in NON-PATENT DOCUMENTS 3 to 5 and PATENT DOCUMENT 1 isolate and dry 1,4-dinitroimidazole or 2,4-dinitroimidazole and use the compound as the material for synthesizing 2,4-dinitroimidazole or 2-chloro-4-nitroimidazole, respectively.

In these processes, both of 1,4-dinitroimidazole and 2,4-dinitroimidazole should be handled as a dry solid, and when excessive friction or shock is imposed to the dry solid, the compound might be decomposed, ignited or exploded, and accordingly, these processes are not preferable from an aspect of safety in the production.

It is desirable to subject 1,4-dinitroimidazole or 2,4-dinitroimidazole to the reaction of the following step without being isolated and dried from the aspect of safety mentioned above, but in such a case, impurities such as by-products generated upon producing each compounds will also present respectively in the following step. Such impurities which might contaminate the final compounds 2-chloro-4-nitroimidazole and 2-bromo-4-nitroimidazole mainly include 4-nitroimidazole, which remain as an unreacted raw material in the production of 1,4-dinitroimidazole or which is generated by hydrolysis of 1,4-dinitroimidazole. Since 2-chloro-4-nitroimidazole and 2-bromo-4-nitroimidazole are used as pharmaceutical intermediates, contamination of the impurities such as by-products should be avoided.

Under the circumstances mentioned above, an object of the present invention is to provide a production process of 2-halo-4-nitroimidazole from 4-nitroimidazole safely while reducing the risks such as decomposition and/or explosion.

Besides, another object is to provide a production process of 2-halo-4-nitroimidazole from 4-nitroimidazole safely and at a high purity while reducing the risks such as decomposition and/or explosion.

Thirdly, according to the process described in NON-PATENT DOCUMENT 3, the yield of 2-chloro-4-nitroimidazole, which is the object compound, is as low as 67%, and such a low yield is unfavorable for the production on an industrial scale, and accordingly, further improvement in the yield is demanded.

Actually, when the present inventors conducted the chlorination reaction of 2,4-dinitroimidazole with concentrated hydrochloric acid according to the process described in NON-PATENT DOCUMENT 3, and then cooled the reaction liquid for a long time at 0° C. or lower for improving the yield, no significant improvement in the yield was observed, and rather limit of the improvement in the yield by cooling was confirmed.

Under the circumstances, an object of the present invention is to provide a production process of 2-halo-4-nitroimidazole simply and at a high yield in a production process of 2-halo-4-nitroimidazole by subjecting 2,4-dinitroimidazole to a halogenation reaction with a halogenating agent.

Forthly, 4-Nitroimidazole is dissolved in acetic acid and then a nitric acid having a high concentration as much as 80 mass % or more and acetic anhydride are added thereto to produce 1,4-dinitroimidazole in any of the processes described in the documents mentioned above.

Actually, when the present inventors conducted production of 1,4-dinitroimidazole according to the processes described in the documents mentioned above, solids deposited upon adding dropwise nitric acid to an acetic acid solution of 4-nitroimidazole, which made a slurry state having a high viscosity and in company with this, excessive load was imposed on the stirring blades and the situations of breakage of the stirring blades and termination of the stirring occurred.

Besides, it is anticipated that when acetic anhydride is added dropwise to this slurry state, stirring cannot be surely performed and local nitration reaction may occur, which may locally cause a large amount of reaction heat. The present inventors estimated heat stability of 1,4-dinitroimidazole by differential scanning calorimetry DSC, and the results revealed that the decomposition starting temperature of 1,4-dinitroimidazole was 156° C., which means that 1,4-dinitroimidazole has a significantly low decomposition temperature and thus poor heat stability compared with a common nitro compound. Therefore, when a large amount of reaction heat is locally caused, 1,4-dinitroimidazole, which has a significantly poor heat stability, may cause self-decomposition which in turn may lead to ignition and explosion.

Furthermore, it becomes difficult to produce 1,4-dinitroimidazole industrially because when the concentration of nitric acid exceeds 70 mass %, the oxidative power thereof is excessively strong and materials of the tubing, the pumps and the containers tends to be limited. In addition, nitric acid having a concentration of more than 70 mass % may generate gases harmful to human body such as nitrogen monoxide gas and nitrogen dioxide gas, which is not preferable in an aspect of handling.

In order to circumvent these problems, the present inventor conducted nitration reaction of 4-nitroimidazole using nitric acid having a concentration of mass % or less in substitution for the nitric acid having a high concentration as high as 80 mass % or more in the conventional processes described in the documents mentioned above, the yield of 1,4-dinitroimidazole remarkably decreased.

Under the circumstances, an object of the present invention is to provide a production process of 1,4-dinitroimidazole safely and at a high yield without using nitric acid having a high concentration which has a high oxidative power and harmful properties and is inappropriate in industrial production.

Fifthly, the temperature of the mixed solution of imidazole at 0° C. to 40° C., nitric acid and concentrated sulfuric acid is allowed to increase to 75° C. or more in the processes for production of 4-nitroimidazole described in the documents mentioned above. In these processes the nitration reaction of imidazole may abruptly proceeds during a process when the temperature elevates to above 75° C. and the reaction heat thereof may further elevates the temperature abruptly, which may lead to a runaway reaction.

Actually, when the present inventors conducted small-scale production according to the process of the documents mentioned above, the nitration reaction of imidazole abruptly proceeded in the halfway of a process when the temperature elevated to above 75° C. in the addition of imidazole, nitric acid and concentrated sulfuric acid, and a runaway phenomenon was observed in which the temperature of the reaction liquid was uncontrollable.

In the case where the temperature of the reaction liquid became thus uncontrollable, the temperature of the reaction liquid may reach the boiling point of nitric acid or concentrated sulfuric acid, and may cause sudden generation of a large quantity of acid gas which may lead to danger such as explosion.

Under the circumstances, an object of the present invention is to provide a production process of 4-nitroimidazole safely without causing abrupt reactions in a production process of 4-nitroimidazole by subjecting imidazole to nitration reaction.

Solution to Problem

The object of the present invention is achieved with a process for the production of a compound of formula (I)

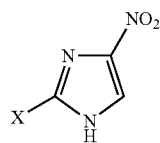
(I)

wherein X is Cl or Br, comprising the steps of:

(i) nitration of a compound of formula (II)

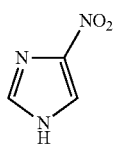
(II)

to obtain a compound of formula (III)

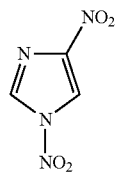
(III)

with the aid of nitric acid in a mixture of acetic acid and acetic anhydride (ii) thermally rearranging the compound of formula (III) into a compound of formula (IV)

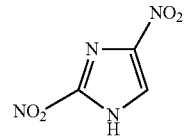
(IV)

(iii) reacting the compound of formula (IV) with a chlorinating or bromating agent.

Preferred embodiments comprise one or more of the following features.

According to an embodiment, the process is continuous.

According to an embodiment, the process further comprises after step (i) the extraction of 1,4-dinitroimidazole, preferably with dichloromethane.

According to an embodiment, the process further comprises after step (i) the quenching, preferably with an ionic aqueous solution.

According to an embodiment, quenching and extracting are performed simultaneously.

According to an embodiment, the thermal rearrangement reaction temperature is between 100 and 150° C., preferably between 120 and 130° C., more preferably 125° C.

According to an embodiment, the thermal rearrangement is performed in chlorobenzene under reflux.

According to an embodiment, the chlorinating agent is hydrochloric acid.

According to an embodiment, the bromating agent is hydrobromic acid.

According to an embodiment, step (i) is followed by successive washings of the reaction mixture.

According to an embodiment, step (iii) is performed at a temperature between 60 and 150° C., preferably 100 and 110° C.

Another object of the invention is a process for the production of an antitubercular agent which comprises the steps of:

(i) nitration of a compound of formula (II) to obtain a compound of formula (III) with the aid of nitric acid in a mixture of acetic acid and acetic anhydride (ii) thermally rearranging the compound of formula (III) into a compound of formula (IV)

(iii) reacting the compound of formula (IV) with a chlorinating or bromating agent to obtain a compound of formula (I)

(iv) reacting the compound of formula (I) with 2-methyloxiran-2-ylmethyl-4-nitrobenzoate (v) reacting the compound obtained in step (iv) with methanesulfonyl chloride (vi) ring closure of the compound obtained in step (v)

(vii) reacting the compound of step (vi) with a compound of formula RH wherein

to obtain a compound of formula (VII)

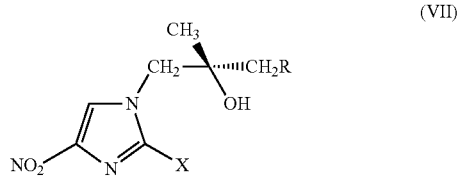

(viii) ring closure of the compound of formula (VII) to obtain a compound of formula (VIII)

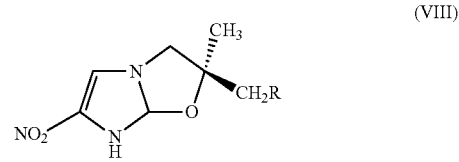

Further features and advantages of the invention will appear from the following description of embodiments of the invention, given as non-limiting examples.

Further, the present inventor has conducted intensive studies to attain the object mentioned above, and consequently has found that 2-halo-4-nitroimidazole can be produced from 4-nitroimidazole safely while reducing the risks such as explosion by a process comprising:

(i) nitrating 4-nitroimidazole to obtain 1,4-dinitroimidazole;

(ii) subjecting the 1,4-dinitroimidazole dissolved in or wetted with a solvent, without isolating or drying operation, to thermal rearrangement reaction to obtain 2,4-dinitroimidazole; and (iii) halogenating the 2,4-dinitroimidazole wetted with a solvent for the thermal rearrangement reaction using a halogenating agent.

That is, the present invention is as follows.

[1]

A production process of 2-halo-4-nitroimidazole comprising:

(i) nitrating 4-nitroimidazole to obtain 1,4-dinitroimidazole;

(ii) subjecting the 1,4-dinitroimidazole dissolved in or wetted with a solvent, without isolating or drying operation, to thermal rearrangement reaction to obtain 2,4-dinitroimidazole; and (iii) halogenating the 2,4-dinitroimidazole wetted with a solvent for the thermal rearrangement reaction using a halogenating agent.

[2]

The production process according to above [1], wherein the process further comprises: (iv) recrystallizing 2-halo-4-nitroimidazole obtained by halogenation of 2,4-dinitroimidazole using water and/or a C3 or lower alcohol as a solvent.

[3]

The production process according to above [2], wherein the step (iv) is a step of dissolving, with heating, 2-halo-4-nitroimidazole in 10 to 40 mass parts of water and/or a C3 or lower alcohol based on 100 mass parts of 2-halo-4-nitroimidazole and then cooling the solution for recrystallization.

[4]

The production process according to any of above [1] to [3], wherein the solvent which 1,4-dinitroimidazole is dissolved in or wetted with in the step (ii) is the same solvent as in the thermal rearrangement reaction.

[5]

The production process according to any of above [1] to [4], wherein the solvent which 1,4-dinitroimidazole is dissolved in or wetted with in the step (ii) is an organic solvent which separates from water and has a boiling point of 95° C. or more.

[6]

The production process according to any of above [1] to [5], wherein the step (iii) is a step of halogenating 2,4-dinitroimidazole wetted with 5 mass parts or more of a solvent for the thermal rearrangement reaction based on 100 mass parts of the 2,4-dinitroimidazole using a halogenating agent.

Further, the present inventor has conducted intensive studies to attain the object mentioned above, and consequently has found that 2-halo-4-nitroimidazole can be surprisingly produced simply and at a high yield by adding water to the reaction liquid after the halogenation reaction of 2,4-dinitroimidazole, and the present inventor has completed the present invention.

That is, the present invention is as follows.

[7]

A production process of 2-halo-4-nitroimidazole by subjecting 2,4-dinitroimidazole to a halogenation reaction with a halogenating agent, wherein the process comprises adding water to reaction liquid after the halogenation reaction to deposit 2-halo-4-nitroimidazole.

[8]

The production process according to above [7], wherein the water is added to the reaction liquid after the halogenation reaction of 2,4-dinitroimidazole in an amount of 25 to 200 mass parts based on 100 mass parts of the halogenating agent used.

[9]

The production process according to above [7] or [8], wherein the halogenating agent is used for the halogenation reaction of 2,4-dinitroimidazole in an amount of 5 to 20 mol for 1 mol of 2,4-dinitroimidazole.

[10]

The production process according to any of above [7] to [9], wherein the halogenating agent is hydrochloric acid or hydrobromic acid.

[11]

The production process according to above [10], wherein the hydrochloric acid has a concentration of 20 to 38 mass %.

[12]

The production process according to above [10], wherein the hydrobromic acid has a concentration of 20 to 49 mass %.

Furthermore, The present inventor has conducted intensive studies to attain the object mentioned above, and the invention has been accomplished upon finding that 1,4-dinitroimidazole can be produced safely and at a high yield without using nitric acid having a high concentration by a production process of 1,4-dinitroimidazole comprising subjecting 4-nitroimidazole to nitration reaction, wherein 4-nitroimidazole is nitrated with acetic anhydride and nitric acid having a concentration of 50 to 70 mass %.

That is, the present invention is as follows.

[13]

A production process of 1,4-dinitroimidazole comprising subjecting 4-nitroimidazole to nitration reaction, wherein 4-nitroimidazole is nitrated with acetic anhydride and nitric acid having a concentration of 50 to 70 mass %.

[14]

The production process of 1,4-dinitroimidazole according to above [13], wherein the acetic anhydride is used in an amount of 2.5 to 22.5 mol for 1 mol of the nitric acid.

[15]

The production process of 1,4-dinitroimidazole according to above [13] or [14], wherein the nitric acid is used in an amount of 1 to 5 mol for 1 mol of the 4-nitroimidazole.

The production process of 1,4-dinitroimidazole according to any of above [13] to [15], wherein the nitration reaction is performed at a reaction temperature of 15 to 30° C.

Furthermore, the present inventor has conducted intensive studies to attain the object mentioned above, and consequently has found that 4-nitroimidazole can be produced safely without causing abrupt reactions by a production process of 4-nitroimidazole comprising subjecting imidazole to nitration reaction, wherein the nitration reaction is performed by warming a sulfuric acid solution of imidazole to 65 to 110° C. and then adding nitric acid thereto or the nitration reaction is performed by warming a nitric acid solution of imidazole to 65 to 110° C. and then adding sulfuric acid thereto, and has thus completed the present invention.

That is, the present invention is as follows.

[17]

A production process of 4-nitroimidazole comprising subjecting imidazole to nitration reaction, wherein the nitration reaction is performed by warming a sulfuric acid solution of imidazole to 65 to 110° C. and then adding nitric acid thereto or the nitration reaction is performed by warming a nitric acid solution of imidazole to 65 to 110° C. and then adding sulfuric acid thereto.

The production process of 4-nitroimidazole according to above [17], wherein sulfuric acid or nitric acid in which imidazole is dissolved before warming has an amount of 2.5 to 5 mol for 1 mol of imidazole.

[19]

The production process of 4-nitroimidazole according to above [17] or [18], wherein the sulfuric acid has a concentration of 95 to 100 mass %.

[20]

The production process of 4-nitroimidazole according to any of above [17] to [19], wherein the nitric acid has a concentration of 50 to 70 mass %.

[21]

The production process of 4-nitroimidazole according to any of above [17] to [20], wherein sulfuric acid or nitric acid which is added to the sulfuric acid solution or nitric acid solution of imidazole after warming has an amount of 0.5 to 1.0 mol for 1 mol of sulfuric acid or nitric acid in which imidazole is dissolved before warming.

Advantageous Effects of Invention

According to the present invention, 2-halo-4-nitroimidazole can be more efficiently produced from 4-nitroimidazole than conventional methods.

According to the present invention, 2-halo-4-nitroimidazole can be produced from 4-nitroimidazole safely while reducing the risks such as decomposition and/or explosion.

Besides, 2-halo-4-nitroimidazole can be produced at a high purity from 4-nitroimidazole safely while reducing the risks such as decomposition and/or explosion.

Further, according to the present invention, a production process of 2-halo-4-nitroimidazole simply and at a high yield in a production process of 2-halo-4-nitroimidazole by subjecting 2,4-dinitroimidazole to a halogenation reaction with a halogenating agent can be provided.

Furthermore, according to the present invention, a production process of 1,4-dinitroimidazole safely and at a high yield without using nitric acid having a high concentration which has a high oxidative power and harmful properties and is inappropriate in industrial production can be provided in a production process of 1,4-dinitroimidazole which comprises subjecting 4-nitroimidazole to nitration reaction.

Furthermore, according to the present invention, a production process of 4-nitroimidazole safely without causing abrupt reactions in a production process of 4-nitroimidazole by subjecting imidazole to nitration reaction can be provided.

DESCRIPTION OF EMBODIMENTS

In the following, the best mode for carrying out the present invention (hereinbelow referred to as the present embodiment) is described in detail. It should be noted that the present invention is not limited to the following embodiment but the present invention can be variously modified and carried out within the gist thereof.

A Process for the Production of 2-halo-4-nitroimidazole 1

The present invention relates to a process for the production of a compound of formula (I)

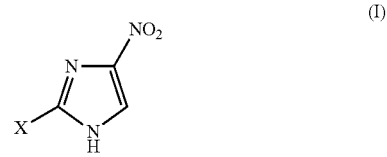

wherein X is Cl or Br.

This process comprises the step (i) of nitrating a compound of formula (II)

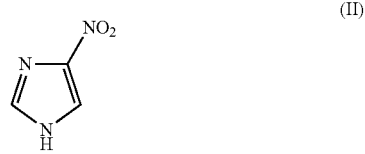

to obtain a compound of formula (III)

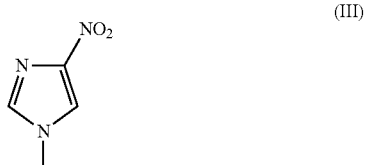

The nitration is performed with the aid of nitric acid. Nitric acid can be added in a molar ratio of 4-nitroimidazole over nitric acid from 1:1 to 1:4, preferably from 1:1 to 1:2, more preferably in a ratio of about 1:1.5.

The nitration is performed in a mixture of suitable solvents, acetic acid and acetic anhydride. The molar ratio acetic anhydride/acetic acid is comprised between 3:1 and 1:10, preferably between 1:1 and 1:5, more preferably between 1:2 and 1:3.

The reaction is performed at a pressure comprised between 0.01 bar and 20 bar, preferably between 0.1 and 5 bar, more preferably between 0.5 and 2 bar, even more preferably under atmospheric pressure. The temperature of the reaction is comprised between 5 and 30° C., preferably between 20 and 25° C.

To stop the reaction, the reaction mixture can be quenched, for example with the addition of water or of an aqueous solution of NaCl.

Preferably, the mixture is quenched with an ionic aqueous solution as a quenching solution. More preferably, aqueous solutions of salts with high solubility in water are used. Salts that can be used are for example KCl, $CaCl_2$, or NaBr.

The resulting compound of formula (III) can be extracted or precipitated from the reaction mixture.

Preferably, the resulting compound is extracted. The extraction can be done with the aid of any suitable solvent or mixture of solvents. Preferably, the solvent is not miscible with water. For example, the solvent is chlorobenzene. Preferably, the extraction solvent is xylene in combination with butyl acetate. More preferably, the solvent is xylene in combination with 10% (% volume) Butyl acetate. As an alternative, the solvent is dichloromethane.

Preferably, the reaction mixture is quenched then extracted, or quenched and extracted simultaneously, i.e. in a same step of the process.

The salts of the quenching solution force the compounds of formula (III) to go into the extraction solvent.

The extracted mixture can be washed with the aid of one or more suitable solutions.

The extracted mixture solution can be washed with an aqueous solution, for example an aqueous solution of sodium chloride. As an alternative, the extracted mixture is washed with an aqueous solution of sodium hydrogen carbonate. As an alternative, the extracted mixture is washed with water.

Preferably, the extracted mixture is neutralized. In particular, the mixture is neutralized by the addition of a suitable base. The base can be an organic or inorganic base. For example, sodium hydroxide or potassium hydroxide can be used.

Preferably, the pH at the end of the neutralization is comprised between 6 and 9, more preferably between 7 and 8.

Preferably, the temperature of the neutralization reaction does not exceed about 30° C. so as to avoid self-degradation of the product. The neutralization is exothermic thus the temperature of the mixture is preferably controlled and regulated. Any suitable regulation devices can be used. For example, a cooler can be used. After the neutralization, the organic and aqueous phases are separated.

Preferably the extracted mixture is washed once or by successive washings, with the same or different solutions.

For example, the mixture can be washed with an aqueous solution, then neutralized and at last washed with another aqueous solution.

The extracted mixture can be neutralized, then washed with an aqueous solution, then washed with water.

Preferably, the extracted solution is neutralized with a solution of NaOH, washed with an aqueous solution of $NaHCO_3$, then washed with water.

The extraction solvent can be removed prior to the step immediately following. In another embodiment it can be only partly removed, for example 20 to 90%, preferably 30 to 70% by volume, and the solvent of the next step is added and then the mixture of the two solvents is distilled to remove the extraction solvent.

The process also comprises the step of thermally rearranging the compound of formula (III) into a compound of formula (IV)

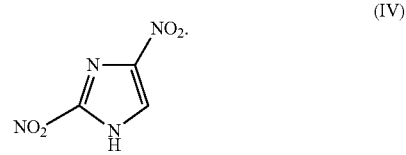 [SMILES: O=[N+]([O-])c1c[nH]c([N+](=O)[O-])n1]

Preferably, the solvent resulting from the extraction process is partly removed. The solvent can be partly removed by any suitable method of separation. Preferably the solvent is distilled. For example, if the extraction solvent is dichloromethane, the solvent can be distilled at 40° C. at atmospheric pressure.

Preferably, the water content of the solution is controlled. Preferably, it does not exceed 500 ppm so as to avoid any unwanted by-product. In particular, by-products due to the back reaction of 4-nitroimidazole with water could be produced. If necessary water can be removed by any suitable methods, preferably water is removed during the distillation of the extraction solvent if there is any.

If necessary, the water removal needs to be done before the rearrangement reaction starts.

The thermal rearrangement reaction can be performed in any suitable solvent or mixture of solvents. For example, the solvent is chlorobenzene, toluene or xylene. Preferably, the solvent is chlorobenzene.

The temperature of the reaction is comprised between 45 and 130° C. Preferably, the temperature is comprised between 100 and 130° C., more preferably the temperature is about 125° C.

The reaction is performed at a pressure comprised between 0.01 bar and 20 bar, preferably between 0.1 and 5 bar, more preferably between 0.5 and 2 bar, even more preferably under atmospheric pressure.

Preferably, the thermal rearrangement is performed under reflux.

The resulting compound can then be separated from the reaction mixture. Any suitable method for separating the compound can be used. For example, the compound can be precipitated or extracted by a suitable solvent.

Preferably, the compound is precipitated by cooling the solution to a temperature at which the compound of formula (IV) precipitates, preferably at a temperature between 0 and 5° C. Then the solution is filtered.

The process also comprises the step of reacting the compound of formula (IV) with a chlorinating or bromating agent.

The chlorination agent can be any suitable chlorinating agent. For example, hydrochloric acid or phosphoryl chloride can be used. Preferably, hydrochloric acid is used.

The bromating agent can be any suitable bromating agent. For example, hydrobromic acid, bromine, or N-bromosuccinimide can be used. Preferably, hydrobromic acid is used.

The reaction temperature is comprised between 40 and 160° C. Preferably, the temperature is comprises between 80 and 120° C. More preferably, the temperature is comprised between 100 and 110° C.

The reaction is performed at a pressure comprised between 0.01 bar and 20 bar, preferably between 0.1 and 5 bar, more preferably between 0.5 and 2 bar, even more preferably under atmospheric pressure.

The resulting compound of formula (I) can be separated from the reaction mixture. It can be extracted or filtered off.

The process can be a continuous process or a batch process. Preferably, the process is a continuous process.

Preferably, the reactants are fed in a continuous stream. The resultant products are withdrawn in a continuous way. Alternatively, the reactant may be fed as intermittent or pulsed streams and/or the products may be withdrawn as intermittent or pulsed streams.

A continuous process is simpler to carry out and more efficient than a batch process.

Then the compound of formula (I) can be used to manufacture an antimicrobial agent.

The manufacture of an antimicrobial agent starting from the compound of formula (I) is described in European Patent Application EP-A-1555267. The antimicrobial agent can be any compound described in EP-A-1555267 and in particular compounds this invention.

Preferably, the antimicrobial agent is a compound of formula (VIII)

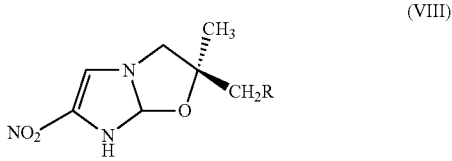

R corresponding to $(CH_2)_n R_2$, n being 1 and $R_2$ having the meaning given above.

The manufacture of the antiomicrobial agent, with the compound of formula I, can be performed according to any process as known in the art and in particular according to the process as defined in EP-A-1555267 and in particular the processes of this invention.

To produce (R)-2-methyl-6-nitro-2-{4-[4-(4-trifluoromethoxyphenoxy)piperidin-1-yl]phenoxymethyl}-2,3-dihydroimidazo[2,1-b]oxazole starting from 2-bromo-4-nitroimidazole, reference is made also especially to examples 3, 4, 6 and 129 of European Patent Application EP-A-1555267.

A Process for the Production of 2-halo-4-nitroimidazole 2

The production process of 2-halo-4-nitroimidazole of the present embodiment is a production process of 2-halo-4-nitroimidazole comprising (i) nitrating 4-nitroimidazole to obtain 1,4-dinitroimidazole; (ii) subjecting the 1,4-dinitroimidazole dissolved in or wetted with a solvent, without isolating or drying operation, to thermal rearrangement reaction to obtain 2,4-dinitroimidazole; and (iii) halogenating the 2,4-dinitroimidazole wetted with a solvent for the thermal rearrangement reaction using a halogenating agent.

The production process of the present embodiment is a process according to a scheme represented by the following formula (2).

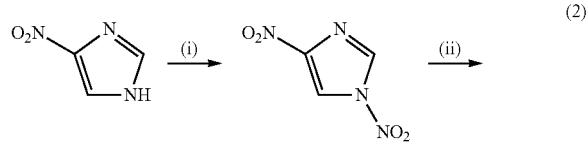

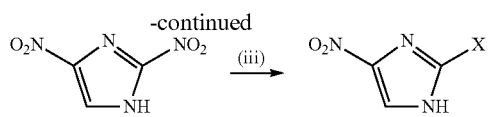

(wherein, X represents a halogen atom.)

Here, the halogen atom represented by X means either one of a fluorine atom, a chlorine atom, a bromine atom or an iodine atom.

The respective steps are described in the following.

[Step (1)]

Step (i) is a step for nitrating 4-nitroimidazole to obtain 1,4-dinitroimidazole. Specific procedure in this step includes, without particular limitation, the following 4 processes:

(1) A process by dissolving and/or suspending 4-nitroimidazole in acetic anhydride and then adding dropwise thereto nitric acid to perform nitration reaction;

(2) a process by dissolving and/or suspending 4-nitroimidazole in nitric acid and then adding dropwise acetic anhydride thereto to perform nitration reaction;

(3) a process by adding 4-nitroimidazole to a mixed solution of acetic anhydride and nitric acid to perform nitration reaction; and (4) a process by dissolving and/or suspending 4-nitroimidazole in acetic acid and then adding dropwise thereto a mixed solution of acetic anhydride and nitric acid to perform nitration reaction.

The nitric acid is used in at least equimolecular amount and preferably 1 to 5 mol for 1 mol of 4-nitroimidazole. The concentration of nitric acid is preferably 50 to 100 mass %, more preferably 50 to 70 mass %, still preferably 65 to 70 mass %.

The acetic anhydride is used in at least equimolecular amount and preferably 2.5 to 22.5 mol, more preferably 4 to 10 mol for 1 mol of the nitric acid.

The used amount of acetic acid for dissolving 4-nitroimidazole is typically around 0 to 10 mol for 1 mol of 4-nitroimidazole.

The reaction temperature for performing the nitration reaction is typically around 0 to 30° C., and preferably 15 to 30° C. The reaction time of the nitration reaction is typically around 1 to 10 hours.

After the nitration reaction, the reaction liquid is added into iced water and extracted with an organic solvent. Subsequently, the organic layer is neutralized with an alkaline aqueous solution, and then the organic layer is separated and dehydrated with a dehydrating agent.

The organic solvent used for extraction (hereinbelow also referred to as an extracting solvent) is not limited particularly as long as it dissolves 1,4-dinitroimidazole, and is not compatible with water and separates therefrom, dichloromethane, chloroform, diethyl ether, etc. can be suitably used since they readily extract 1,4-dinitroimidazole and separate from water well.

The extracting solvent is preferably an organic solvent having a boiling point of 95° C. or more. When the boiling point of the extracting solvent is 95° C. or more, it can be heated at 95° C. which is the temperature necessary for thermal rearrangement of 1,4-dinitroimidazole to 2,4-dinitroimidazole. Therefore, the extracting solvent can be used as it is as a solvent to be used for thermal rearrangement reaction of step (ii) described below. Examples of the organic solvent having a boiling point of 95° C. or more include chlorobenzene, o-xylene, m-xylene, p-xylene, toluene, ethylbenzene, dibutyl ether, octanol.

As for the alkaline aqueous solution used for the neutralization of the organic layer, alkalescence aqueous solutions such as a saturated sodium hydrogen carbonate aqueous solution are preferably used from a viewpoint of suppressing decomposition of 1,4-dinitroimidazole.

The dehydrating agent is not limited particularly as long as it does not affect 1,4-dinitroimidazole and adsorbs moisture in the organic solvent and can be removed by filtration, and commonly used dehydrating agents such as magnesium sulfate and molecular sieves can be used.

[Step (ii)]

Step (ii) is a step for subjecting 1,4-dinitroimidazole dissolved in or wetted with a solvent, without isolating or drying operation, to thermal rearrangement reaction to obtain 2,4-dinitroimidazole.

As stated above, when the boiling point of the extracting solvent is 95° C. or more, it can be heated at 95° C. which is the temperature necessary for thermal rearrangement of 1,4-dinitroimidazole to 2,4-dinitroimidazole. Therefore, the extracting solvent can be used as it is as a solvent to be used for thermal rearrangement reaction of (ii) described below without using another solvent.

When the extracting solvent has a boiling point of 95° C. or less, the extracting solvent is evaporated to such an extent that 1,4-dinitroimidazole is not dried to solid, and a solvent having a boiling point of 95° C. or more is added so that 1,4-dinitroimidazole is dissolved and/or suspended therein, and then the thermal rearrangement reaction is conducted.

The reaction temperature in the thermal rearrangement is typically 95 to 130° C., preferably 100 to 125° C. It is preferable that the amount of the solvent in the thermal rearrangement reaction is more than the amount for allowing 1,4-dinitroimidazole to be completely dissolved.

The thus resultant 2,4-dinitroimidazole can be obtained by concentrating the reaction liquid and filtering the solids, and Step (iii), the following step, is conducted without drying 2,4-dinitroimidazole but rather keeping 2,4-dinitroimidazole wetted with the solvent of the thermal rearrangement reaction.

[Step (iii)]

Step (iii) is a step for halogenating 2,4-dinitroimidazole wetted with a solvent for the thermal rearrangement reaction using a halogenating agent.

2,4-Dinitroimidazole wetted with an organic solvent for the thermal rearrangement reaction is treated with a halogenating agent, and thus 2-halo-4-nitroimidazole can be obtained more safely as compared with the conventional processes.

The "condition that 2,4-dinitroimidazole is wetted with an solvent for the thermal rearrangement reaction" preferably means a condition that 5 or more mass parts of the solvent is contained per 100 mass parts of 2,4-dinitroimidazole. When the solvent is contained in an amount of 5 or more mass parts per 100 mass parts of 2,4-dinitroimidazole, both the friction sensitivity and the drop-hammer sensitivity of 2,4-dinitroimidazole according to JIS K 4810 become 8th grade, which is less sensitive as compared with the friction sensitivity of and the drop-hammer sensitivity of 6th grade and 7th grade respectively of 2,4-dinitroimidazole in a dried condition, and therefore, 2-halo-4-nitroimidazole can be produced more safely.

The impurities contaminating 2-halo-4-nitroimidazole in the present embodiment will be present in a higher content as shown in Table 2 when 1,4-dinitroimidazole and 2,4-dinitroimidazole are subjected to the following step without in isolating or drying operation as compared with the case where 1,4-dinitroimidazole and 2,4-dinitroimidazole are isolated and dried. However, contamination with 4-nitroimidazole can be suppressed and 2-halo-4-nitroimidazole can be obtained at a high purity by using hydrochloric acid and hydrobromic acid as a halogenating agent of the halogenation of 2,4-dinitroimidazole, and further dissolving, with heating, the resultant 2-halo-4-nitroimidazole in water or a solvent of C3 or lower alcohols and then cooling the mixture for recrystallization.

TABLE 2

|  | "Prior art" (Proceed to next steps after isolation and dry an intermediate) | "Embodiment of the present invention" (Proceed next steps without isolation and dry an intermediate) |
| --- | --- | --- |
| The contamination rate of 4-nitroimidazole (I) contaminated in the process step of 2,4-dinitroimidazole (III) (The amount of (I)/ the amount of (II) [%]) | 0.63% ((I) in solid (II)) | 1.37% ((I) in solution (II)) |
| The contamination rate of 4-nitroimidazole (I) contaminated in theprocess step of 2-chloro-4-nitroimidazole (IV) (The amount of (I)/ the amount of (III) [%]) | 1.23% ((I) in solid (III)) | 2.60% ((I) in solution (III)) |
| The contamination rate of 4-nitroimidazole (I) contaminated in a final product 2-chloro-4-nitroimidazole (IV) (The amount of (I)/ the amount of (IV) [%]) | 0% ((I) in solid (IV)) | 0% ((I) in solid (IV)) |

Specific examples of the object compound 2-halo-4-nitroimidazole include 2-fluoro-4-nitroimidazole, 2-chloro-4-nitroimidazole, 2-bromo-4-nitroimidazole and 2-iodo-4-nitroimidazole.

The halogenating agent is not limited in particular, and in case of producing 2-fluoro-4-nitroimidazole as the object compound, hydrofluoric acid, etc. can be used; in case of producing 2-chloro-4-nitroimidazole as the object compound, hydrochloric acid, phosphoryl chloride, thionyl chloride, chlorine, 2-chloroethanol, etc. can be used; in case of producing 2-bromo-4-nitroimidazole as the object compound, hydrobromic acid, bromine, etc. can be used; and in case of producing 2-iodo-4-nitroimidazole as the object compound, hydroiodic acid, iodine, etc. can be used.

When the halogenating agent to be used for the halogenation reaction is hydrochloric acid, the concentration of hydrochloric acid is preferably 20 to 38 mass %, more preferably 30 to 36 mass %. The hydrochloric acid is used preferably in an amount of 5 to 50 mol, more preferably 10 to 30 mol for 1 mol of 2,4-dinitroimidazole. The reaction temperature of the chloridization reaction is typically 80 to 120° C., more preferably 90 to 110° C. The reaction time is typically 0.5 to 10 hours.

When the halogenating agent to be used for the halogenation reaction is hydrobromic acid, the concentration of hydrobromic acid is preferably 20 to 49 mass %, more preferably 45 to 49 mass %. The hydrobromic acid is used preferably in an amount of 10 to 30 mol for 1 mol of 2,4-dinitroimidazole. The reaction temperature of the bromination reaction is typically 80 to 140° C., more preferably 100 to 120° C. from the aspects of reactivity, selectivity. The reaction time is typically 0.5 to 5 hours, more preferably 1 to 3 hours from the aspects of reactivity, selectivity.

As for the isolation process of 2-halo-4-nitroimidazole obtained by the production process of the present embodiment, a process of cooling the halogenation reaction liquid followed by filtration, washing and drying, a process of cooling the halogenation reaction liquid followed by neutralization, filtration, washing and drying and a process of adding water to the halogenation reaction liquid followed by filtration, washing and drying can be used.

[Step (iv)]

In addition, in the production process of the present embodiment, a step (iv) of recrystallizing 2-halo-4-nitroimidazole obtained after the halogenation of the 2,4-dinitroimidazole using water and/or a C3 or lower alcohol as a solvent may be further included.

2-Halo-4-nitroimidazole having a higher purity can be obtained by recrystallizing 2-halo-4-nitroimidazole by warming and dissolving 2-halo-4-nitroimidazole in water and/or a C3 or lower alcohol as a solvent and then cooling, and further performing filtration, washing and drying as needed.

The amount of water and/or a C3 or lower alcohol for recrystallization is preferably 10 to 40 mass parts for 100 mass parts of 2-halo-4-nitroimidazole. Decrease in the yield associated with recrystallization can be controlled at the minimum when the amount of water and/or the C3 or lower alcohol is in the range mentioned above.

The temperature for dissolving with heating is preferably 60 to 100° C., and the cooling temperature is preferably 0 to 20° C. The filtrate after the filtration can substitute the solvent for recrystallizing 2-halo-4-nitroimidazole produced in the other batch.

Since the filtrate is a saturated aqueous solution of 2-halo-4-nitroimidazole, decrease in the yield can be suppressed by using the filtrate as the solvent for recrystallizing 2-halo-4-nitroimidazole produced in the other batch.

A Process for the Production of 2-halo-4-nitroimidazole 3

The production process of 2-halo-4-nitroimidazole of the present embodiment is a production process of 2-halo-4-nitroimidazole by subjecting 2,4-dinitroimidazole to a halogenation reaction with a halogenating agent, wherein the process comprises adding water to reaction liquid after the halogenation reaction to deposit 2-halo-4-nitroimidazole.

The production process of the present embodiment is a process according to the scheme represented by the following formula (3):

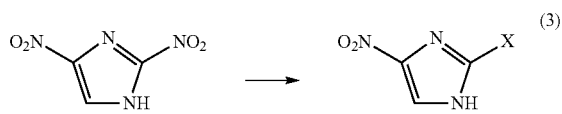

(3)

wherein X represents a halogen atom.

Here, the halogen atom represented by X means either one of a fluorine atom, a chlorine atom, a bromine atom or an iodine atom.

Specific examples of 2-halo-4-nitroimidazole, which is the object compound, include 2-fluoro-4-nitroimidazole, 2-chloro-4-nitroimidazole, 2-bromo-4-nitroimidazole and 2-iodo-4-nitroimidazole.

The halogenating agent in the present embodiment is not limited in particular, and in case of producing 2-fluoro-4-nitroimidazole as the object compound, hydrofluoric acid, etc. can be used; in case of producing 2-chloro-4-nitroimidazole as the object compound, hydrochloric acid, phosphorus oxychloride, thionyl chloride, chlorine, 2-chloroethanol, etc. can be used; in case of producing 2-bromo-4-nitroimidazole as the object compound, hydrobromic acid, bromine, etc. can be used; and in case of producing 2-iodo-4-nitroimidazole as the object compound, hydroiodic acid, iodine, etc. can be used.

When the halogenating agent to be used for the halogenation reaction is hydrochloric acid, the concentration of hydrochloric acid is preferably 20 to 38 mass %, more preferably 30 to 36 mass %. When the concentration of hydrochloric acid is less than 20 mass %, the halogenation reaction proceeds only slowly and the yield tends to decrease, and when the concentration of hydrochloric acid exceeds 38 mass %, the boiling point of the hydrochloric acid decreases and therefore the halogenation reaction becomes hard to proceed and the yield tends to decrease. When the halogenating agent is hydrobromic acid, the concentration of hydrobromic acid is preferably 20 to 49 mass %, more preferably 45 to 49 mass %. When the concentration of hydrobromic acid is less than 20 mass %, the halogenation reaction proceeds only slowly and the yield tends to decrease, and when the concentration of hydrobromic acid exceeds 49 mass %, the boiling point of the hydrobromic acid decreases and therefore the halogenation reaction becomes hard to proceed and the yield tends to decrease.

The halogenating agent to be used for halogenation reaction is preferably 5 to 20 mol, more preferably 12 to 20 mol for 1 mol of 2,4-dinitroimidazole. When the halogenating agent is used in an amount less than 5 mol, the halogenation reaction proceeds only slowly and the yield tends to decrease. When the halogenating agent is used in an amount more than 20 mol, the yield tends to decrease due to increase in the amount of 2-halo-4-nitroimidazole which dissolves in the halogenating agent.

The reaction temperature for performing the halogenation reaction is typically 80 to 120° C., preferably 90 to 110° C. The reaction time is typically 0.5 to 10 hours.

The amount of water to be added to the reaction liquid after the halogenation reaction is preferably 25 to 200 mass parts, more preferably 65 to 125 mass parts, and still more preferably 75 to 115 mass parts based on 100 mass parts of the used halogenating agent. When the amount of water is less than 25 mass parts, the concentration of the halogenating agent in the reaction liquid becomes high, 2-halo-4-nitroimidazole dissolves in the reaction liquid, and the yield tends to decrease. On the other hand, when the amount of water is more than 200 mass parts, 2-halo-4-nitroimidazole dissolves in the reaction liquid due to the increase of the fluid volume, and the yield tends to decrease.

The reaction liquid may be cooled after water is added to the reaction liquid. The cooling temperature for cooling is typically 0 to 25° C., and preferably 0 to 10° C.

As for the isolation process of 2-halo-4-nitroimidazole obtained by the production process of the present embodiment, a process of cooling the reaction liquid followed by filtration, washing and drying, a process of cooling the reaction liquid followed by neutralization, filtration, washing and drying can be used.

A Process for the Production of 1,4-dinitroimidazole

The production process of 1,4-dinitroimidazole of the present embodiment is a production process of 1,4-dinitroimidazole comprising subjecting 4-nitroimidazole to nitration reaction, wherein 4-nitroimidazole is nitrated with acetic anhydride and nitric acid having a concentration of 50 to 70 mass %.

In the production process of the present embodiment, acetyl nitrate, which is a nitrating agent, is generated from acetic anhydride and nitric acid and this is reacted with 4-nitroimidazole performing nitration reaction to produce 1,4-dinitroimidazole.

Since acetic anhydride reacts with water contained in nitric acid and accordingly it is effective in suppressing decomposition by water of acetyl nitrate which is a nitrating agent and 1,4-dinitroimidazole which is the object compound, and as a result, can improve the yield of 1,4-dinitroimidazole.

Specific procedure in the production process of the present embodiment includes, without particular limitation, the following four processes:

(1) A process by dissolving and/or suspending 4-nitroimidazole in acetic anhydride and then adding dropwise thereto nitric acid having a concentration of 50 to 70 mass % to perform nitration reaction; (2) a process by dissolving and/or suspending 4-nitroimidazole in nitric acid having a concentration of 50 to 70 mass % and then adding dropwise acetic anhydride thereto to perform nitration reaction; (3) a process by adding 4-nitroimidazole to a mixed solution of acetic anhydride and nitric acid having a concentration of 50 to 70 mass % to perform nitration reaction; and (4) a process by dissolving and/or suspending 4-nitroimidazole in acetic acid and then adding dropwise thereto a mixed solution of acetic anhydride and nitric acid having a concentration of 50 to 70 mass % to perform nitration reaction.

The concentration of nitric acid to be used in the production process of the present embodiment is 50 to 70 mass %, preferably 65 to 70 mass %. When the concentration of nitric acid is less than 50 mass %, the nitration reaction proceeds only slowly and the yield tends to decrease and when the concentration of nitric acid exceeds 70 mass %, a slurry state is generated during the reaction, thereby a large amount of reaction heat may be locally caused.

Preferably acetic anhydride is used in an amount of 2.5 to 22.5 mol, more preferably 4 to 10 mol for 1 mol of the nitric acid. When the acetic anhydride is used in an amount less than 2.5 mol, acetyl nitrate which is a nitrating agent is decomposed with moisture contained in nitric acid, the yield tends to decrease. When the acetic anhydride is used in an amount more than 22.5 mol, the yield tends to decrease due to increase in the amount of the reaction solution.

The nitric acid is used in at least equimolecular amount and preferably 1 to 5 mol for 1 mol of 4-nitroimidazole. When the used amount of nitric acid is less than 1 time mol, the yield tends to decrease, and when the used amount of nitric acid exceeds 5 mol, the yield tends to decrease due to increase in the amount of the reaction solution.

The reaction temperature for performing the nitration reaction is preferably 15° C. to 30° C. When the reaction temperature is less than 15° C., explosive acetyl nitrate, slow in reaction rate, may remain unreacted in the system, which is unpreferable. In the meantime, when the reaction temperature exceeds 30° C., decomposition of acetyl nitrate is promoted, and the yield tends to decrease. The reaction time of the nitration reaction is typically around 1 to 10 hours.

The thus obtained 1,4-dinitroimidazole can be isolated, for example, by adding an organic solvent and an alkaline aqueous solution to the reaction to separate the reaction liquid, and obtaining the organic layer followed by subjecting the obtained organic layer to concentration and drying to solids.

A Process for the Production of 4-nitroimidazole

The production process of 4-nitroimidazole of the present embodiment is a production process of 4-nitroimidazole comprising subjecting imidazole to nitration reaction, wherein the nitration reaction is performed by warming a sulfuric acid solution of imidazole to 65 to 110° C. and then adding nitric acid thereto or the nitration reaction is performed by warming a nitric acid solution of imidazole to 65 to 110° C. and then adding sulfuric acid thereto.

The nitration reaction for producing 4-nitroimidazole from imidazole is an exothermic reaction. In the processes of NON-PATENT DOCUMENT 4 and NON-PATENT DOCUMENT 5 mentioned above, all the raw materials are made into one solution and the temperature thereof is elevated for producing 4-nitroimidazole, and therefore, all the amount of imidazole may cause nitration reaction with generation of heat at a time, thus generate a large amount of heat, and make the reaction temperature uncontrollable, which may lead to a runaway reaction.

In contrast, in the production process of the present embodiment, the nitration reaction is performed by warming a sulfuric acid solution of imidazole to 65 to 110° C. and then adding nitric acid thereto or the nitration reaction is performed by warming a nitric acid solution of imidazole to 65 to 110° C. and then adding sulfuric acid thereto, and accordingly, nitration of imidazole slowly proceeds only with the added amount of nitric acid or sulfuric acid after warming and thus the reaction can be controlled appropriately. Therefore, 4-nitroimidazole can be produced safely without causing sudden reactions.

The nitration reaction is performed by warming a sulfuric acid or nitric acid solution in which imidazole is dissolved to 65 to 110° C., preferably 70 to 90° C., and then adding nitric acid or sulfuric acid thereto in the production process of the present embodiment. When the temperature of the sulfuric acid or nitric acid solution of imidazole is less than 65° C., the reaction rate of the nitration reaction becomes slow, which means that nitric acid is not consumed immediately, and a large amount of imidazole and nitric acid will remain unreacted. As a result, when the mixture is warmed, control of the reaction temperature might not be possible as in the conventional processes. On the other hand, when the temperature of the sulfuric acid or nitric acid solution of imidazole exceeds 110° C., heat decomposition of nitric acid may occur and the yield of 4-nitroimidazole tends to decrease.

Sulfuric acid or nitric acid in which imidazole before warming is dissolved is preferably 2.5 to 5 mol, more preferably 3 to 4 mol for 1 mol of imidazole. When the sulfuric acid or nitric acid is used in an amount less than 2.5 mol, the nitration reaction tends to proceed slowly. When the sulfuric acid or nitric acid is used in an amount more than 5 mol, the yield tends to decrease due to increase in the amount of the ammonium water for neutralization to be added to the solution in which 4-nitroimidazole is dissolved.

The method for adding nitric acid or sulfuric acid to the sulfuric acid of or nitric acid solution of imidazole is not limited particularly as long as the reaction can be controlled appropriately, but sequential addition to the reaction system is preferable and dropwise addition to the reaction system is more preferable. The "sequential addition" as used herein means continuous or discontinuous addition by portions of an amount of nitric acid or sulfuric acid which is necessary for the reaction while allowing the reaction to be controlled.

The concentration of sulfuric acid used in the production process of the present embodiment is preferably 95 to 100 mass %, more preferably 97 to 100 mass %. When the concentration of sulfuric acid is less than 95 mass %, the nitration reaction tends to proceed slowly.

The concentration of nitric acid used in the production process of the present embodiment is preferably 50 to 70 mass %, more preferably 65 to 70 mass %. When the concentration of nitric acid is less than 50 mass %, the nitration reaction tends to proceed slowly, and the yield of 4-nitroimidazole tends to decrease. When the concentration of nitric acid exceeds 70 mass %, the oxidative power thereof is excessively strong and materials of the tubing, pumps and container for solution sending or storage tends to be limited. In addition, gases harmful to human body such as nitrogen monoxide gas and nitrogen dioxide gas may be generated, which is not preferable in an aspect of handling.

The sulfuric acid or nitric acid which is added to the sulfuric acid solution or nitric acid solution of imidazole after warming is preferably 0.5 to 2.0 mol, more preferably 0.8 to 1.2 mol for 1 mol of the sulfuric acid or nitric acid in which imidazole is dissolved before warming. When the sulfuric acid or nitric acid is used in an amount less than 0.5 mol or more than 2.0 mol, the yield tends to decrease.

After nitric acid or sulfuric acid is added to a sulfuric acid or nitric acid solution of imidazole, the reaction temperature of typically around 80° C. to 100° C., preferably 90° C. to 100° C. is kept to continue the nitration reaction for around 1 to 10 hours.

The thus obtained 4-nitroimidazole can be isolated, for example, by adding iced water, an alkaline aqueous solution to the reaction liquid followed by filtration, washing and drying.

EXAMPLES

Examples which specifically describe the present embodiment are exemplified in the following, but the present embodiment is not limited to the following examples unless it departs from the gist thereof.

All equivalents (eq.) are molar equivalents and calculated relative to the starting material 4-nitroimidazole.

Example 1

Step 1

In a first vessel 1.00 eq. of 4-Nitroimidazole (solid) is mixed with 2.01 eq. acetic anhydride and 5.83 eq. acetic acid. The mixture is cooled down to 15° C. Into this suspension 1.5 eq. nitric acid is dosed. The reaction is weakly exothermic and it has to be ensured that the temperature of the reaction mixture is not exceeding 15° C. After the addition of nitric acid the reaction mixture is warmed up to 23-25° C. and is stirred for 3 hours. After stirring of about 2 hours a yellow-orange solution appears.

In a second vessel 69.72 eq. water and 7.35 eq. sodium chloride were mixed and stirred at ambient temperature until all sodium chloride is dissolved. 19.17 eq. dichloromethane is added. Afterwards the two-phase mixture is cooled to 15° C.

The reaction mixture of the first vessel is dosed into the stirred vessel (second vessel). The quench is weakly exothermic and it has to be ensured not to exceed 20° C. After dosing the content of the second vessel is stirred for 30 minutes, afterwards the phases were separated. The upper aqueous phase is waste whereas the lower organic phase contains the product 1,4-dinitroimidazole and remains in the second vessel.

Sometimes an intermediate third phase appears between the two phases and shall stay in the second vessel with the lower organic phase.

For neutralization 18.51 eq. of 35% (w/w, weight over weight) sodium hydroxide is dosed into the second vessel. The neutralization reaction is exothermic therefore it has to be ensured not to exceed 30° C. This workup step is critical because temperatures above 30° C. are leading to self-accelerated degradation of 1,4-dinitroimidazole. The pH at the end of neutralization is between 7 and 8.

After dosing the content of the second vessel is stirred for 30 minutes, afterwards the phases were separated. The upper aqueous phase is waste whereas the lower organic phase contains 1,4-dinitroimidazole and remains in the second vessel. The phase separation is good. The upper aqueous phase is of dark red to yellow brown color. The intermediate phase has disappeared.

3.25 eq. of an aqueous solution 5% (w/w) sodium hydrogen carbonate solution is added to the second vessel. A weak gas evolution is observed. The content of the second vessel is stirred for 30 minutes. Afterwards the phases are separated. The upper aqueous phase is waste whereas the lower organic phase contains 1,4-dinitroimidazole and remains in the second vessel. The separation is good. The upper aqueous phase is of yellow color.

14.60 eq. water is added to the second vessel. The content of the second vessel is stirred for 30 minutes. Afterwards the phases were separated. The upper aqueous phase is wasted whereas the lower organic phase contains 1,4-dinitroimidazole and remains in the second vessel. The phase separation is good. The upper aqueous phase is of light yellow color.

Step 2

In the second vessel 1,4-dinitroimidazole dissolved in dichloromethane is distilled at ambient temperature. The inner temperature in the vessel is 40° C., and the temperature of the exhaust vapor is 38-41° C.

The water content in the residue is limited to 500 ppm. If necessary a water/dichloromethane hetero-azeotrope has to be removed until the water content in the residue is below 500 ppm. The water content is controlled by Karl Fisher method.

Half of the dichloromethane is removed by distillation until solid starts to precipitate. The dichloromethane distillate can be recycled. Quality of the dichloromethane can be controlled by refraction index ($n_{D20}$<=1,426 corresponds with dichloromethane content>=95% (w/w)).

11.12 eq. chlorobenzene is added in the second vessel and the distillation is continued at ambient temperature. The temperature in the second vessel is 45-126° C., the temperature of the exhaust vapor is 32-120° C. At head temperature up to 50° C. the distillate can be recycled. Above 50° C. the distillate is waste. Control of the dichloromethane content is done by diffraction index. The distillate is light brown, and nitrous gases are formed.

After the solvent exchange the mixture in the second vessel is stirred 7 hours at 125° C. under reflux to perform the rearrangement reaction. After 6 hours a first in-process control can be taken, >99.0% conversion to 2,4-dinitroimidazole should be achieved.

The reaction mixture is cooled down to 0-2° C. and is stirred at this temperature for 1 hour. The precipitated 2,4-dinitroimidazole is filtered. The mother liquor color is orange.

The filter cake is washed with 1.29 eq. chlorobenzene. It has to be taken care that the filter cake is not dried at this step because the solid 2,4-dinitroimidazole is shock and friction sensitive. An amount of 10-15% (w/w) residual chlorobenzene is sufficient for phlegmatizing.

The product of step 2 is wet 2,4-dinitroimidazole with 96% (w/w) content (Yield: 67%).

Step 3

To produce 2-chloro-4-nitroimidazole

In a third vessel 3 eq. 2,4-dinitroimidazole wet with chlorobenzene is mixed with 11.0 eq. of a 37% (w/w) hydrochloric acid and water. The suspension is heated to 105° C.

The distillation begins at a temperature of 70-80° C. Water, chlorobenzene and hydrochloric acid are distilled during heating up the reaction mixture to 105° C.

When the temperature of 105° C. is reached, the mixture is stirred at 105° C. for 7 hours. The conversion should be >98%. The heating to 105° C. has to be performed carefully because the mixture tends to foam.

After the reaction the mixture is cooled down to 10° C. and the precipitate is filtered off.

The filter cake is washed with 2.09 eq. water in three portions and dried under vacuum at 45° C. until the loss of drying is <=0.5% (w/w).

The product is 2-chloro-4-nitroimidazole (Yield 65-80%, Purity>98%).

To produce 2-bromo-4-nitroimidazole

In a third vessel 1 eq. 2,4-dinitroimidazole wet with chlorobenzene is mixed with 15.96 eq. of a 47% (w/w) hydrobromic acid and 1.5 eq. urea. The suspension is heated to 105° C.

The distillation begins at a temperature of 70-80° C. Water, chlorobenzene and hydrobromic acid are distilled during heating up the reaction mixture to 105° C.

When the temperature of 105° C. is reached, the mixture is stirred at 105° C. for 14 hours. The conversion should be >98%.

After the reaction the mixture is cooled down to 0° C. and the precipitate is filtered off.

The filter cake is washed with 77.22 eq. water in three portions and dried under vacuum at 40-50° C. until the loss of drying is <=0.5% (w/w).

Example 2-1

Production of 1,4-dinitroimidazole and 2,4-dinitroimidazole

After 20 g of 4-nitroimidazole was put in a flask, 36.4 mL of acetic acid was added thereto and while the temperature of the reaction solution was kept below 20° C., 14.6 mL of 97 mass % nitric acid was added dropwise thereto. After the dropwise addition of nitric acid was completed, 36.4 mL of acetic anhydride was added dropwise thereto and after the temperature of the reaction solution elevated to 25° C., the resultant mixture was allowed to react for 3 hours. After the reaction ended, the reaction solution was added into 100 g of iced water. Extraction with 100 mL of methylene chloride was performed three times and this organic layer was washed twice with 100 mL of a saturated sodium hydrogen carbonate aqueous solution. The organic layer was separated and 30 g of magnesium sulfate was added thereto for dehydration to obtain 1,4-dinitroimidazole as a dichloromethane solution. Subsequently, the solvent was evaporated with an evaporator to such an extent that the solution was not dried to solid and then 300 mL of chlorobenzene was added thereto, and the solution was heated to 125° C. and allowed to react for 24 hours so as to perform conversion to 2,4-dinitroimidazole. After the reaction ended, the deposited solid was filtered to obtain 25.3 g of 2,4-dinitroimidazole as a solid wetted with chlorobenzene (wetted with 10 mass % of chlorobenzene, yield 82.3%). This was identified to be 2,4-dinitroimidazole by IR absorption spectrum (KBr): 3147, 1550, 1509, 1340, 1107 cm$^{-1}$ $^1$H-NMR spectrum (DMSO-d$_6$) δ ppm: 8.53 (s, 1H), 9.98 (br, s, 1H)

Example 2-2

Alternate Process

Production of 1,4-dinitroimidazole and 2,4-dinitroimidazole

After 20 g of 4-nitroimidazole was put in a flask, 36.4 mL of acetic acid was added thereto and while the temperature of the reaction solution was kept below 20° C., 14.6 mL of 97 mass % nitric acid was added dropwise thereto. After the dropwise addition of nitric acid was completed, 36.4 mL of acetic anhydride was added dropwise thereto and after the temperature of the reaction solution elevated to 25° C., the resultant mixture was allowed to react for 3 hours. After the reaction ended, the reaction solution was added into 100 g of iced water. Extraction with 100 mL of p-xylene was performed four times and this organic layer was washed twice with 100 mL of a saturated sodium hydrogen carbonate aqueous solution. The organic layer was separated and 30 g of magnesium sulfate was added thereto for dehydration to obtain 1,4-dinitroimidazole as a p-xylene solution. Subsequently, the solvent was evaporated with an evaporator to about two third amount, and the solution was heated to 125° C. and allowed to react for 24 hours so as to perform conversion to 2,4-dinitroimidazole. After the reaction ended, the deposited solid was filtered to obtain 24.1 g of 2,4-dinitroimidazole as a solid wetted with p-xylene (wetted with 15 mass % of p-xylene, yield 74.9%). This was identified to be 2,4-dinitroimidazole by IR absorption spectrum (KBr): 3147, 1550, 1509, 1340, 1107 cm$^{-1}$ $^1$H-NMR spectrum (DMSO-d$_6$) δppm: 8.53 (s, 1H), 9.98 (br, s, 1H)

Example 3-1

Production of 2-chloro-4-nitroimidazole 65.8 g of 2,4-Dinitroimidazole wetted with chlorobenzene (wetted with 31 mass % of chlorobenzene) was added to 660 mL of 35 mass % of hydrochloric acid and the temperature of the reaction liquid was elevated to 100° C. and reacted for 5 hours. After the reaction ended, the solution was cooled for crystallization. After the crystals were filtered, the crystals were heated and dissolved in 930 mL of water at 90° C. and 33.0 g of 2-chloro-4-nitroimidazole (yield 70.7%) (HPLC purity 97.6%) was obtained by cooling, filtration and drying. This was identified to be 2-chloro-4-nitroimidazole by IR absorption spectrum (KBr): 3152, 1556, 1510, 1473, 1405, 1375, 1194, 1092, 822 cm$^{-1}$ $^1$H-NMR spectrum (DMSO-d$_6$) δppm: 8.42 (s, 1H), 14.2 (br, s, 1H)

Example 3-2

Alternate Process

Production of 2-bromo-4-nitroimidazole 2033.5 g of 49 mass % hydrobromic acid was added dropwise to 145.6 g of 2,4-dinitroimidazole wetted with p-xylene (wetted with 12 mass % of p-xylene). The temperature of the reaction liquid was elevated to 100° C. and reacted for 5 hours. After the reaction ended, the reaction liquid was gradually neutralized with 2000 mL of a saturated sodium hydrogen carbonate aqueous solution while the solution was cooled to deposit crystals. After the crystals were filtered, the crystals were heated and dissolved in 3000 mL of water at 95° C. and 75.0 g of 2-bromo-4-nitroimidazole (yield 47.6%) (HPLC purity 100%) was obtained by cooling, filtration and drying. This was identified to be 2-bromo-4-nitroimidazole by IR absorption spectrum (KBr): 3209, 3146, 1547, 1514, 1453, 1390, 1084, 823 cm$^{-1}$ $^1$H-NMR spectrum (DMSO-d$_6$) δppm: 8.43 (s, 1H)

Example 4

Production of 2-chloro-4-nitroimidazole 5.0 g of 2,4-dinitroimidazole (purity 92.3%) was added to 30 mL of 35 mass % hydrochloric acid. The reaction liquid was warmed to 95° C. and the reaction was performed for 7 hours. After the reaction, 43 g of water was added and the resultant mixture was cooled to 0° C. for crystallization. The crystals were filtered and dried to obtain 3.31 g of 2-chloro-4-nitroimidazole (yield 77.1%). This was identified to be 2-chloro-4-nitroimidazole by IR absorption spectrum (KBr): 3152, 1556, 1510, 1473, 1405, 1375, 1194, 1092, 822 cm$^{-1}$ $^1$H-NMR spectrum (DMSO-d$_6$) δppm: 8.42 (s, 1H), 14.2 (br, s, 1H).

Comparative Example 1

5.0 g of 2,4-dinitroimidazole (purity 92.3%) was added to 62 mL of 35 mass % hydrochloric acid. The reaction liquid was warmed to 95° C. and the reaction was performed for 7 hours. After the reaction, the reaction mixture was cooled to 0° C. for crystallization. The crystals were filtered and dried to obtain 2.88 g of 2-chloro-4-nitroimidazole (yield 67.1%).

Example 5

After 20 g of 4-nitroimidazole was put in a flask, 144.5 mL of acetic anhydride was added thereto and while the temperature was kept at 25° C., 14.5 mL of 69 mass % nitric acid was added dropwise thereto. After the addition of nitric acid was completed, the resultant mixture was stirred at 25° C. for 3 hours. The reaction solution was added into 100 g of iced water and extracted with 300 mL of dichloromethane. The organic layer was washed with 300 mL of a saturated sodium hydrogen carbonate aqueous solution and dried over 30 g of magnesium sulfate. The organic layer was filtered and the solvent was evaporated under reduced pressure to obtain 21 g of 1,4-dinitroimidazole (yield 75.1%).

IR absorption spectrum (KBr): 3147, 1550, 1509, 1340, 1107 cm$^{-1}$ $^1$H-NMR spectrum (DMSO-d$_6$) δppm: 8.53 (s, 1H), 9.98 (br, s, 1H)

Example 6

After 60 mL of 95 mass % concentrated sulfuric acid was put in a flask, 20 g of imidazole was added thereto and completely dissolved. A sulfuric acid solution of imidazole was warmed to 70° C. and 60 mL of 69 mass % nitric acid was added dropwise thereto. After the addition of nitric acid was completed, the temperature of the resultant mixture was elevated to 100° C. and the mixture was stirred for 5 hours. The reaction solution was added into of 100 g of iced water, the mixture was neutralized with 25 mass % ammonia water. Filtration, washing and drying were further performed to give 26 g of 4-nitroimidazole (yield 78.2%), which was identified to be 4-nitroimidazole by IR absorption spectrum (KBr): 3141, 3012, 2883, 2821, 1557, 1510, 1496, 1431, 1383, 1253, 991, 868 cm$^{-1}$ $^1$H-NMR spectrum (DMSO-d$_6$) δppm: 7.83 (s, 1H), 8.30 (s, 1H), 13.1 (br, s, 1H).

INDUSTRIAL APPLICABILITY

The production process of the present invention has industrial applicability in the fields such as explosives and medicinal drugs, in particular.

The invention claimed is:

1. A process for the production of 2-halo-4-nitroimidazole wherein the halogen is Cl or Br, comprising the steps of:
   (i) nitration of 4-nitroimidazole to obtain 1,4-dinitroimidazole with the aid of nitric acid in a mixture of acetic acid and acetic anhydride;
   (ii) thermally rearranging 1,4-dinitroimidazole into 2,4-dinitroimidazole without isolating and drying operations; and
   (iii) reacting 2,4-dinitroimidazole wetted with a solvent with a chlorinating or bromating agent to obtain 2-halo-4-nitroimidazole.

2. The process according to claim 1, which is continuous.

3. The process according to claim 1, which further comprises after step (i) extraction of 1,4-dinitroimidazole.

4. The process according to claim 1, which further comprises after step (i) quenching.

5. The process according to claim 3 or 4, wherein quenching and extracting are performed simultaneously.

6. The process according to claim 1, in which the thermal rearrangement temperature is between 100 and 150° C.

7. The process according to claim 1, wherein the thermal rearrangement is performed in chlorobenzene under reflux.

8. The process according to claim 1, wherein the chlorinating agent is hydrochloric acid.

9. The process according to claim 1, wherein the bromating agent is hydrobromic acid.

10. The process according to claim 1, wherein step (i) is followed by successive washings of the mixture.

11. The process according to claim 1, wherein step (iii) is performed at a temperature between 60 and 150° C.

12. The process according to claim 1, wherein step (i) is followed by a quenching step which is performed at a temperature between 60 and 150° C.

13. The process for the production of an antitubercular agent which comprises the steps of:
   (i) nitration of 4-nitroimidazole to obtain 1,4-dinitroimidazole with the aid of nitric acid in a mixture of acetic acid and acetic anhydride;
   (ii) thermally rearranging 1,4-dinitroimidazole into 2,4-dinitroimidazole without isolating and drying operations,
   (iii) reacting 2,4-dinitroimidazole wetted with a solvent with a chlorinating or bromating agent to obtain 2-halo-4-nitroimidazole, wherein the halogen is Cl or Br;
   (iv) reacting 2-halo-4-nitroimidazole with 2-methyloxiran-2-ylmethyl-4-nitrobenzoate;
   (v) reacting the compound obtained in step (iv) with methanesulfonyl chloride;

(vi) ring closure of the compound obtained in step (v);
(vii) reacting the compound of step (vi) with a compound of formula RH wherein

to obtain a compound of formula (VII)

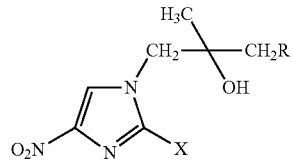

wherein X—Cl or Br; and
(viii) ring closure of the compound of formula (VIII) to obtain a compound of formula (VIII)

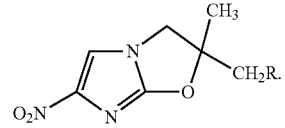

14. A process for the production of 2-halo-4-nitroimidazole comprising the steps of:
  (i) nitrating 4-nitroimidazole in a nitration reaction to obtain 1,4-dinitroimidazole;
  (ii) subjecting the 1,4-dinitroimidazole dissolved in or wetted with a solvent, without an isolating or drying operation, to a thermal rearrangement reaction to obtain 2,4-dinitroimidazole; and
  (iii) subjecting 2,4-dinitroimidazole to a halogenation reaction by halogenating the 2,4-dinitroimidazole wetted with a solvent for the thermal rearrangement reaction using a halogenating agent to obtain 2-halo-4-nitroimidazole.

15. The process according to claim 14, wherein the process further comprises: (iv) recrystallizing the 2-halo-4-nitroimidazole obtained by halogenation of 2,4-dinitroimidazole using water and/or a $C_3$ or lower alcohol as a solvent.

16. The process according to claim 15, wherein the step (iv) is a step of dissolving, with heating, 2-halo-4-nitroimidazole in 10 to 40 mass parts of water and/or a $C_3$ or lower alcohol based on 100 mass parts of 2-halo-4-nitroimidazole and then cooling the solution for recrystallization.

17. The process according to any one of claims 14 to 16, wherein the solvent which 1,4-dinitroimidazole is dissolved in or wetted with in step (ii) is the same solvent as in the thermal rearrangement reaction.

18. The process according to any one of claims 14 to 16, wherein the solvent which 1,4-dinitroimidazole is dissolved in or wetted with in step (ii) is an organic solvent which separates from water and has a boiling point of 95° C. or more.

19. The process according to claim 14, wherein step (iii) is a step of halogenating 2,4-dinitroimidazole wetted with 5 mass parts or more of a solvent for the thermal rearrangement reaction based on 100 mass parts of the 2,4-dinitroimidazole, using a halogenating agent.

20. The process according to claim 14, wherein the process comprises adding water after the halogenation reaction to deposit 2-halo-4-nitroimidazole.

21. The process according to claim 20, wherein the water is added after the halogenation reaction of 2,4-dinitroimidazole in an amount of 25 to 200 mass parts based on 100 mass parts of the halogenating agent.

22. The process according to claim 20, wherein the halogenating agent used for the halogenation reaction of 2,4-dinitroimidazole is in an amount of from 5 to 20 mol for 1 mol of 2,4-dinitroimidazole.

23. The process according to any one of claims 20 to 22, wherein the halogenating agent is hydrochloric acid or hydrobromic acid.

24. The process according to claim 23, wherein the hydrochloric acid has a concentration of 20 to 38 mass %.

25. The process according to claim 23, wherein the hydrobromic acid has a concentration of 20 to 49 mass %.

26. The process according to claim 14, wherein 4-nitroimidazole is nitrated in the nitration reaction with acetic anhydride and nitric acid having a concentration of 50 to 70 mass %.

27. The process according to claim 26, wherein the acetic anhydride is used in an amount of 2.5 to 22.5 mol for 1 mol of the nitric acid.

28. The process according to claim 26 or 27, wherein the nitric acid is used in an amount of from 1 to 5 mol for 1 mol of the 4-nitroimidazole.

29. The process according to claim 26, wherein the nitration reaction is performed at a reaction temperature of 15 to 30° C.

30. The process according to claim 3, wherein the 1,4-dinitroimidazole is extracted with dichloromethane.

31. The process according to claim 4, wherein the quenching is done with an ionic aqueous solution.

32. The process according to claim 6, wherein the reaction temperature is between 120 and 130° C.

33. The process according to claim 32, wherein the reaction temperature is 125° C.

34. The process according to claim 11, wherein the temperature is between 100 and 110° C.

35. The process according to claim 12, wherein the temperature is between 100 and 110° C.

* * * * *